United States Patent [19]

Goldberg

[11] Patent Number: 4,494,085
[45] Date of Patent: Jan. 15, 1985

[54] MINIATURIZED ATOMIC FREQUENCY STANDARD HAVING BOTH FILTER CELL AND ABSORPTION CELL IN RESONATOR CAVITY

[75] Inventor: Seymour Goldberg, Boston, Mass.

[73] Assignee: EG&G, Inc., Wellesley, Mass.

[21] Appl. No.: 372,834

[22] Filed: Apr. 28, 1982

[51] Int. Cl.³ .............................................. H03L 7/26
[52] U.S. Cl. ..................................... 331/94.1; 331/3; 324/304; 324/305
[58] Field of Search ................... 331/94.1, 3; 324/304, 324/305

[56] References Cited

U.S. PATENT DOCUMENTS

| | | | |
|---|---|---|---|
| 3,129,389 | 4/1964 | Packard et al. | 331/3 |
| 3,192,472 | 6/1965 | Bender et al. | 324/58.5 A |
| 3,382,452 | 5/1968 | Rempel et al. | 331/3 |
| 3,390,350 | 6/1968 | Davidovits et al. | 331/94.1 |
| 3,403,349 | 9/1968 | Wieder | 331/94.1 |
| 3,513,381 | 5/1970 | Happer, Jr. | 324/304 |
| 3,798,565 | 3/1974 | Jechart | 331/94.1 |
| 3,903,481 | 9/1975 | Jechart | 331/3 |

FOREIGN PATENT DOCUMENTS

| | | |
|---|---|---|
| 52-19096 | 2/1977 | Japan . |
| 2067751 | 7/1981 | United Kingdom . |

OTHER PUBLICATIONS

Busca et al., "Long-term Frequency Stabilization of the Rb⁸⁷ Maser," 24 IEEE Transactions on Instrumentation and Measurement 291-296, (Dec. 1975).

Mathur et al., "Light Shifts in the Alkali Atoms" Physical Review, vol. 171, No. 1, Jul. 5, 1968, pp. 11-19.

Matsuda et al., "Signal Intensity Characteristics of the $^{87}$Rb Double Resonance Due to the Pumping Light", Japanese J. of Appl. Physics, vol. 16, No. 3, Mar. 1977, pp. 391-396.

Kuramochi et al., "Composite-type $^{87}$Rb Optical-Pumping Light Source", Optics Letters, vol. 6, No. 2, Feb. 1981, pp. 73-75.

Audoin et al., "Atomic Frequency Standards and Clocks", J. of Physics E. Scientific Instruments, vol. 6, No. 9, (1976.09), pp. 697-720.

Primary Examiner—Siegfried H. Grimm
Assistant Examiner—D. C. Mis
Attorney, Agent, or Firm—Finnegan, Henderson, Farabow Garrett & Dunner

[57] ABSTRACT

An optical-physics package used in an atomic frequency standard is miniaturized and the performance thereof improved. The optical-physics package includes a microwave cavity in which is positioned a filter cell and an absorption cell, preferably located in close physical proximity to one another. The microwave cavity may double as an oven, and is preferably designed to operate in the TE111 mode with "E" probe microwave coupling. Dielectric loading is provided by the filter cell and absorption cell to reduce the internal dimensions of the microwave cavity.

13 Claims, 4 Drawing Figures

MINIATURIZED ATOMIC FREQUENCY STANDARD HAVING BOTH FILTER CELL AND ABSORPTION CELL IN RESONATOR CAVITY

BACKGROUND OF THE INVENTION

I. Field of the Invention

The present invention relates to the field of packaging optical and physics-related elements of an atomic frequency standard. More particularly, this invention is directed toward a package of the optical-physics elements of an atomic frequency standard which reduces the size of the package while maintaining effective operation of the package.

II. Description of the Prior Art

Atomic frequency standards or clocks using an optical-physics package are well known. The optical-physics packages of such atomic frequency standards commonly include a microwave cavity, an absorption cell, a light source, and a light detector. In such prior art optical-physics packages, the absorption cell typically contains a vaporous material such as a rubidium isotope $Rb^{87}$ which has at least one absorption line having hyperfine components, such that light having hyperfine components corresponding to the hyperfine components of this absorption line is absorbed, or at least dispersed. The separation of such hyperfine components utilized in rubidium frequency standards is due to a hyperfine transition in the ground state ($5S_{\frac{1}{2}}$) and corresponds to a frequency of 6,834,682,612 hz. This frequency is called the natural hyperfine transition frequency.

The light source of prior art optical-physics packages preferably contains the same vaporous material as the absorption cell, such as the rubidium isotope $Rb^{87}$. In this way, the light source will generate light having the hyperfine components of the absorption cell.

In such prior art devices the degree of absorption is sensed by a light detector, typically a silicon photocell, positioned on the side of the absorption cell opposite to the light source. As a beam of optical pumping light having a particular hyperfine component is absorbed, the degree of such absorption is detected as a decrease in the output of the light detector. However, this optical pumping results in a reduction in atoms having energy corresponding to that hyperfine component, causing the amount of absorption to diminish and the output of the light detector to increase to a steady state level, all of which is well-known to those skilled in the art.

The amount of absorption in such prior art devices is, therefore, additionally affected by placing the absorption cell within a microwave cavity and controlling the frequency of a magnetic field introduced into this cavity. When the magnetic field frequency is the same as the hyperfine transition frequency of the absorption cell, absorption is increased, and the output of the photocell again decreases. Moreover, when this magnetic field is varied to sweep symmetrically above and below the hyperfine transition frequency, the first harmonic output of this sweep frequency disappears from the output of the photocell. Accordingly, a phase-locked amplifier, in prior art devices, is coupled to the output of the photocell and is used to control the frequency of an oscillator which generates the magnetic field to precisely set the oscillator at the hyperfine transition frequency of the $Rb^{87}$ absorption cell.

To obtain a usable signal, such prior art devices may also employ an additional uni-direction homogeneous magnetic field within the cavity; one or more buffer gases in the absorption cell and/or in the light source; and/or extremely accurate temperature control over the absorption cell and the light source.

Some prior art devices further employ a filter cell located between the light source and the absorption cell to attenuate undesirable frequencies of light generated by the light source. When vaporous $Rb^{87}$ is used in the absorption cell, vaporous $Rb^{85}$ may be used in the filter cell. A filter cell also provides a convenient mechanism to offset variations which may occur in the hyperfine transition frequency of the absorption cell with changes in the intensity of the light source. However, the filter cell adds substantially to the size of prior art optical-physics packages.

The internal dimensions of microwave cavities in atomic frequency standards are dictated by the hyperfine transition frequency of the vaporous material within the absorption cell and by the dielectric material within the cavity. Accordingly, for a given absorption material within the absorption cell, namely $Rb^{87}$, and a given amount and type of dielectric material within the microwave cavity, i.e., the dielectric loading within the cavity, there is a given nominal resonant frequency, and therefore a given limitation on the geometric configuration of the resultant cavity. In known prior art devices, substantially the entire interior of the cavity is utilized to house the absorption cell, and the filter cell is positioned to the exterior of the cavity, interposed between the light source and the absorption cell. Moreover, since operation of a filter cell is temperature sensitive, as is operation of the absorption cell, a temperature control oven must be made large enough to house both cells, or separate ovens must be used. Accordingly, the size of the resulting optical-physics package is substantially increased by the use of a filter cell in the prior art.

A substantial advance in the prior art towards miniaturization of optical-physics packages occurred by eliminating the filter cell and instead introducing the absorption material of the filter cell, typically the isotope $Rb^{85}$, into the absorption cell. The resulting hybrid absorption cell operates both as an absorption cell and as a filter cell, thereby eliminating the need for a separate filter cell and its attendant support apparatus.

Nevertheless, this advance in miniaturization led to considerable difficulties in the calibration and maintenance of such hybrid absorption cells. The choice of an absorption cell buffer gas affects the hyperfine transition frequency of the absorption cell. When separate filter and absorption cells are used, a filter cell buffer gas may be used which is different from the buffer gas used in the absorption cell. Thus, when separate filter and absorption cells are used, a filter cell buffer gas which allows for optimum use of the filter cell can be selected without any effect on the hyperfine transition frequency of the absorption cell. This option is lost in the hybrid absorption cell configuration. In addition, the hyperfine transition frequency of an absorption cell is temperature dependent, and this dependence can be controlled to some degree by the buffer gases used in the absorption cell. Obviously, in a hybrid absorption cell any selection of buffer gas to control the filtering aspects of such cell also may affect the stability and location of the hyperfine transition frequency.

It is, therefore, an object of the present invention to provide a novel miniature optical-physics package for use with an atomic frequency standard.

Another object of the present invention is to maintain the benefit of utilizing a filter cell in an optical-physics package of an atomic frequency standard without unduly increasing the size of that package.

It is still another object of the present invention to minimize frequency dependence on temperature in an optical-physics package while reducing the overall size of that package.

Additional objects and advantages of the present invention will be set forth in part in the description which follows, and in part will be obvious from the description or may be learned by practice of the invention. The objects and advantages of the invention may be realized and obtained by means of the instrumentalities and combinations particularly pointed out in the appended claims.

SUMMARY OF THE INVENTION

To achieve the foregoing objects and in accordance with the purposes of the invention as embodied and broadly described herein, there is provided an optical-physics package for use with an atomic frequency standard including a light source, a microwave cavity, and an absorption cell positioned within the cavity to be irradiated by the light source, with this package having the improvement of further comprising a filter cell also located within the microwave cavity between the absorption cell and the light source.

Preferably, the absorption cell of the subject invention has a temperature coefficient opposite in sign to the temperature coefficient of the filter cell, and even more preferably, the absorption cell has a temperature coefficient also equal in magnitude to the temperature coefficient of the filter cell. It is further preferred that the optical-physics package of the subject invention further include collimating means located within the cavity between the absorption cell and the filter cell to uniformly distribute light from the light source onto the absorption cell.

The absorption cell and the filter cell are preferably located in sufficiently close physical proximity to one another within the cavity so that both cells are subjected to essentially the same temperature fluctuations. Moreover, the cavity is preferably designed to operate in the TE111 mode and the walls of the cavity preferably serve as an oven to provide a temperature within the cavity at which temperature the filter cell achieves the zero light shift condition such that the resonant frequency of the absorption cell is independent of the light intensity of the incident light from the light source.

In a more narrow sense, the subject invention may be summarized as an optical-physics package for an atomic frequency standard comprising a microwave cavity operable in the TE111 mode; an absorption cell located within that cavity and containing vaporous $Rb^{87}$; a light source for illuminating the absorption cell to modify the population density of at least one select energy level of the $Rb^{87}$; and a filter cell located within the cavity between the light source and the absorption cell including vaporous $Rb^{85}$ to attenuate selective energy components of the light source.

BRIEF DESCRIPTION OF THE DRAWINGS

The accompanying drawings, which are incorporated in and constitute a part of the specification, illustrate a preferred embodiment of the invention and, together with the description, serve to explain the principles of the invention.

DESCRIPTION OF THE PREFERRED EMBODIMENTS

Reference will now be made in detail to the present preferred embodiment of the invention, an example of which is illustrated in the accompanying drawings.

Figure 1:
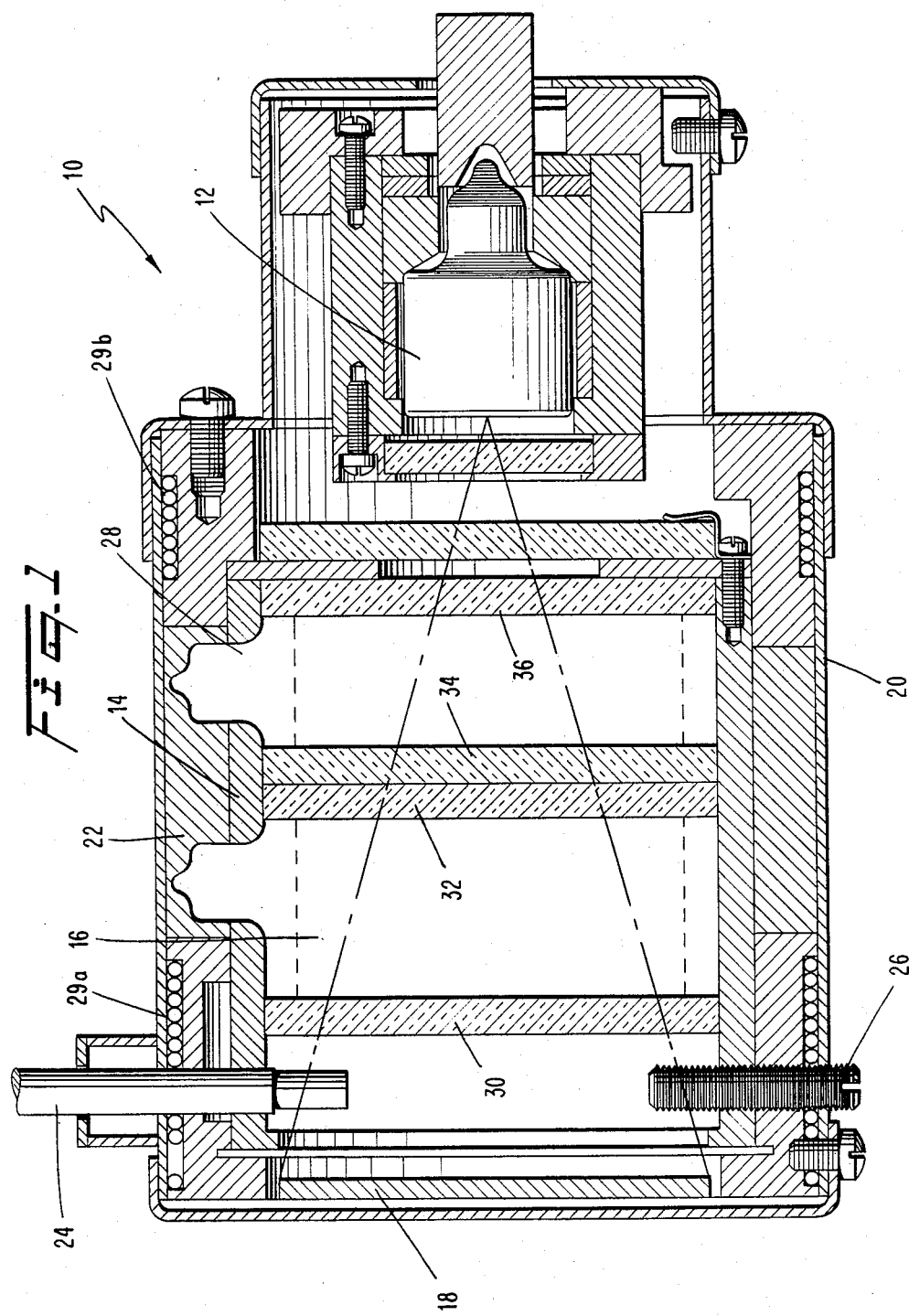
FIG. 1 is a side-section view, greatly enlarged of an optical-physics package incorporating the teachings of the present invention as applied to a rubidium frequency standard.

A preferred embodiment of the optical-physics package is shown in FIG. 1 and is represented generally by numeral 10. This package includes a lamp 12, a microwave cavity 14, an absorption cell 16, a photocell 18, a magnetic shield 20, heating element 22, a microwave input 24, C-field coils 29a and 29b and a tuning screw 26. As embodied herein, lamp 12 preferably contains rubidium in the form of the isotope $Rb^{87}$ and emits photons of characteristic energy required to excite or optically pump absorption cell 16. In order to provide a minimum size configuration of package 10, lamp 12 preferably assumes the form of a miniaturized vapor discharge lamp assembly disclosed in a co-pending application, Ser. No. 372,837, filed concurrently with the subject application by the inventor of the subject application, and entitled VAPOR DISCHARGE LAMP ASSEMBLY, the content of which is hereby incorporated by reference. Of course, other forms of light sources, particularly other more conventional forms of alkali vapor light sources and perhaps even lasers which require the use of a filter cell, may also be employed in accordance with the teachings of the present invention. As is well-known in the art, it is required that the hyperfine components of light emitted by lamp 12 correspond to the hyperfine components of the absorption line of absorption cell 16.

Microwave cavity 14 is provided in package 10 to have, in conjunction with the dielectric loading contained within cavity 14, a resonant frequency which corresponds generally to the hyperfine transition frequency of absorption cell 16. When adapted to operate in the common TE111 mode, which typically permits cavity 14 to assume the smallest cavity dimension for a given frequency, prior art cavities generally assume dimensions on the order of 1.1 inches in diameter and 1.1 inches in length to resonate at the 6834 mhz hyperfine transition frequency for $Rb^{87}$. As will be explained below, it is one function of the present invention to reduce the size of cavity 14 to less than the size of such prior art cavities.

As disclosed herein, the walls of cavity 14 not only define a microwave resonant chamber, but may also provide the structure for an oven which is used to control the temperature of the interior of cavity 14. For this purpose, heater 22 is located in immediate thermal contact to the exterior walls of cavity 14, converting cavity 14 into a microwave cavity-oven.

Absorption cell 16 is positioned within microwave cavity 14 to receive light from lamp 12. Absorption cell 16 is designed to have outer dimensions to fit within cavity 14 in a manner which does not completely fill the interior length of cavity 14. Absorption cell 16 preferably contains a vaporous alkali metal, and more preferably contains the isotope $Rb^{87}$.

As illustrated in FIG. 1, package 10 further includes photocell 18 aligned to receive light radiated from lamp 12 after the light has passed through absorption cell 16. Photocell 18 may, for example, comprise a silicon photocell. Of course, photocell 18 may also take the form of any suitable light detector.

A magnetic shield 20 is shown surrounding cavity 16 and photocell 18 to provide shielding of cavity 14 from external sources of magnetic energy. As illustrated in the preferred embodiment in FIG. 1, heater 22 is positioned intermediate the exterior of cavity 14 and the interior of magnetic shield 20, and in close thermal contact with cavity 14. Heater 22 may, in the alternative, be placed on the exterior of magnetic shield 20, converting magnetic shield 20 into both a magnetic shield and an oven.

As illustrated in FIG. 1, there is also provided a microwave input 24 to cavity 14. Microwave input 24 is shown in FIG. 1 in the form of a probe, thereby providing "E" coupling of microwave energy to the interior of cavity 14. It is to be understood that although the present preferred embodiment of the subject invention incorporates an "E" probe form of coupling, other forms of coupling, such as a loop of wire, also may be used to provide microwave coupling to the interior of cavity 14. Moreover, C-field coils 29a and 29b are also shown in FIG. 1 to provide a substantially uniform D.C. magnetic bias field in cavity 14.

Tuning screw 26 is also illustrated in FIG. 1 as extending into cavity 14 and thereby providing a means for tuning the resonant frequency of cavity 14. It is presently understood that tuning screw 16 may be located as shown in FIG. 1 opposite microwave input 24, or in the alternative, may be located on the same side of cavity 14 a microwave input 24.

In accordance with the present invention, there is provided a filter cell located within a microwave cavity of an optical-physics package for an atomic frequency standard between an absorption cell, also located within that cavity, and a light source for the optical-physics package. This arrangement is designed to provide the benefit of utilizing a filter cell in conjunction with an absorption cell to attenuate undesirable energy components of the incident light, while avoiding the prior art disadvantage of increased package size typically associated with the utilization of a filter cell. Moreover, by positioning at least one window of the filter cell and one window of the absorption cell in an approximate central location within the cavity, the cavity may be dielectrically loaded in a manner which permits reduced overall size of the cavity and still maintains resonance within the cavity at the hyperfine transition frequency of the absorption cell.

The size of the absorption cell, and with it the amount of absorptive material present in the absorption cell, is necessarily reduced to permit the microwave cavity to accommodate the filter cell within the interior of the microwave cavity. To compensate for the reduction in the absolute amount of absorptive material potentially available for exposure to the light incident from the light source, the temperature of the absorption cell may be increased to increase the vapor pressure within the absorption cell and thereby increase the number of rubidium atoms in the vapor state. Moreover, the temperature of the filter cell can be adjusted to achieve a zero light shift condition which eliminates variation of the resonant frequency of the absorption cell with the intensity of light incident from the light source. Still further, by positioning both the absorption cell and the filter cell within the cavity and in close physical proximity to one another and by carefully adjusting the content of the buffer gas within the absorption cell, the absorption cell may be made to have a temperature coefficient equal in magnitude but opposite in sign to the temperature coefficient of the filter cell, thereby minimizing the overall temperature coefficient of the resultant optical-physics package, while yet providing a miniaturized form of such package.

Accordingly, as illustrated in FIG. 1 by way of example and not limitation, there is provided a filter cell 28 within the interior of microwave cavity 14 and in close physical and, hence, thermal proximity to absorption cell 16. With absorption cell 16 containing $Rb^{87}$ it is preferable that filter cell 28 contain $Rb^{85}$. Accordingly, while absorption cell 16 is illuminated by lamp 12 to modify the population density of at least one select energy level of the $Rb^{87}$ within absorption cell 16, filter cell 28 operates to attenuate selective energy components of lamp 12, thereby permitting absorption cell 16 to be illuminated predominately by light from lamp 12 corresponding to a particular hyperfine component of absorption cell 16.

Moreover, filter cell 28 may provide a convenient mechanism to minimize the temperature coefficient of optical-physics package 10. The temperature coefficient of optical-physics package 10 is minimized by balancing the typical negative temperature coefficient of filter cell 28 against the typical positive temperature coefficient of absorption cell 16. For example, when absorption cell 16 contains $Rb^{87}$ and includes a buffer gas comprising a nitrogen-argon mixture in the ratio of about 1.1/1.0 nitrogen atoms to argon atoms at a pressure of about 10 torr, the temperature coefficient of the resonant frequency of such an absorption cell is approximately $+1 \times 10^{-10}$ parts per degree centigrade. This means that for every one degree centigrade variation in temperature of the absorption cell, the resultant variation in the resonant frequency of the absorption cell will be an increase equal to the characteristic resonant frequency of the absorption material multiplied by the temperature coefficient, which coefficient in the foregoing example is about $+1 \times 10^{-10}$. Thus in the foregoing example, and given the nominal resonant frequency of an $Rb^{87}$ absorption cell as 6,834,682,612 hz, the frequency variation of the absorption cell for a one degree centigrade variation in temperature of the absorption cell would be 6,834,682,612 times $+1 \times 10^{-10}$, or 0.6834 hz.

Similarly, for a filter cell 28 incorporating $Rb^{85}$ and a buffer gas component of argon at approximately 120 torr, or a nitrogen-argon mixture in approximately the proportions of 1.1 atoms of nitrogen to 1.0 atom of argon, then for an operating light intensity of lamp 12 providing a yield of approximately 100 microamps at the output of silicon photocell 18, the temperature coefficient of filter cell 28 is on the order of $-1 \times 10^{-10}$ parts per degree centigrade. Thus, positioning of filter cell 28 within cavity 14, provides not only for a reduction in the size of microwave cavity 14, and hence a reduction in the size of the overall package 10, but facilitates the balancing of temperature coefficients of absorption cell 16 and filter cell 28 to improve the performance of the overall package 10 by minimizing the temperature dependent frequency variation of the nominal resonant frequency of the absorption cell.

As illustrated in FIG. 1, absorption cell 16 has dielectric windows 30 and 32 through which light may pass, and filter cell 28 has dielectric windows 34 and 36 also through which light may pass. Dielectric windows 32 and 34 are located approximately central to cavity 14. Windows 32 and 34, accordingly, provide dielectric loading near the center of cavity 14. This dielectric loading permits the interior dimensions of cavity 14 to be reduced while maintaining resonance at the hyperfine transition frequency of $Rb^{87}$. For example, using the teachings of the present invention, the interior dimensions of cavity 14 may be reduced from the typical 1.1 inch in diameter by 1.1 inch in length requirements for resonance at 6,834 mhz, to a size of approximately 0.81 inches in diameter and 1.1 inches in length, and yet maintain resonance at the 6,834 mhz frequency.

To compensate for the reduced size of absorption cell 16, cavity 14 may be operated at a higher temperature than normally employed. The higher temperature increases the vapor pressure of the rubidium in absorption cell 16 and thereby increases the number of rubidium atoms in the vapor state. For example, heater 22 may be operated to maintain the temperature within cavity 14 at about 70 to 80 degrees centigrade to provide vaporous $Rb^{87}$ at a partial pressure of about $10^{-5}$ torr within absorption cell 16. It is then possible to select a buffer gas and the length of filter cell 28 to achieve a "zero light shift" operating point, which is an operating point wherein the frequency standard of package 10 is made substantially independent of changes in the light intensity of lamp 12, thus allowing for stabilization of the hyperfine transition frequency. A filter cell containing nearly pure $Rb^{85}$ and 120 torr of argon buffer gas and having an internal length of 0.25 inches is found to result in a zero light shift at 77 degrees centigrade. This temperature may be maintained within cavity 14 by the operation of heating element 22, which, for example, may take the form of a resistance heater. The use of such a relatively high operating temperature is also ideal for allowing operation of package 10 in an environment characterized by elevated ambient temperatures.

Figure 2:
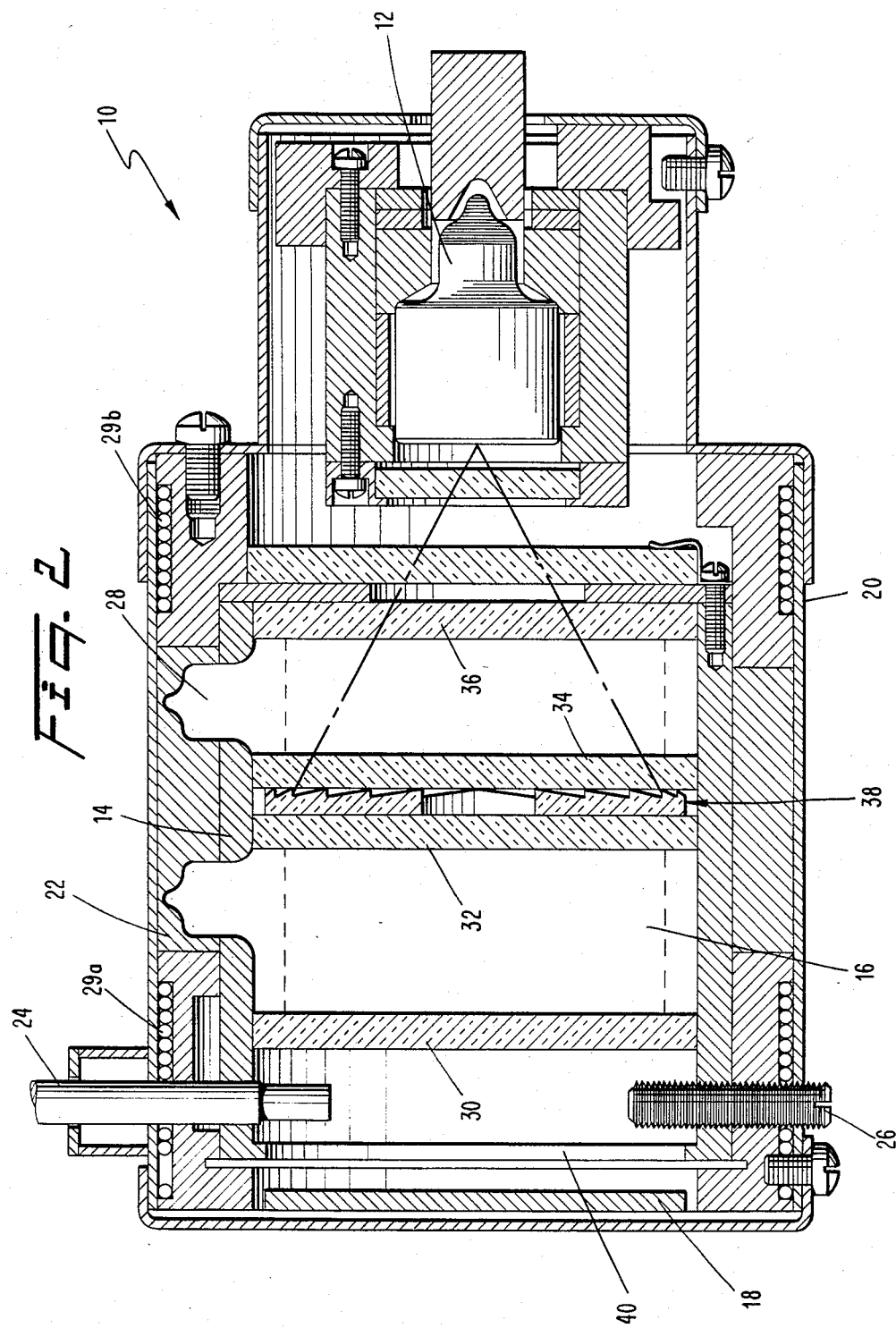
FIG. 2 shows a side view of another apparatus incorporating the teachings of the invention.

In order to increase still further the efficiency of the optical-physics package of the subject invention, there may be provided, in accordance with the teachings of the present invention, collimating means located within the cavity between the absorption cell and the filter cell to direct the light from the light source into the absorption cell on a path parallel to the shortest path through the absorption cell to the photocell. As illustrated in FIG. 2, in which elements common to those shown in FIG. 1 are numbered as in FIG. 1, a collimating lens 38 is positioned within cavity 14 between absorption cell 16 and filter cell 28. Collimating lens 38 may, for example, take the form of a Fresnel lens which improves the performance of optical-physics package 10 by collimating the light before it passes through the absorption cell to be either absorbed or passed through to the photocell 18.

Lamp 12 typically emits diverging cones of rays from any point on its surface, causing the light intensity at the entrance window 32 of absorption cell 16 to far exceed that at exit window 30 of absorption cell 16. Since a shift in frequency of the narrow absorption line of absorption cell 16 is proportional to the intensity of light striking absorption cell 16, it is highly desirable for the incident beam of light to be as uniform as possible. An additional advantage of collimating lens 38 is that a large increase of efficiency of utilization of light emitted by lamp 12 is obtained due to the large solid angle of rays collected by lens 38. Moreover, the dielectric material in the lens contributes to the desirable dielectric loading effect within the cavity 14.

A second collimating lens 40 may be positioned between absorption cell 16 and photocell 18 in order to focus the beam of light passing through absorption cell 16 onto the smaller sized photocell 18.

Figure 3:
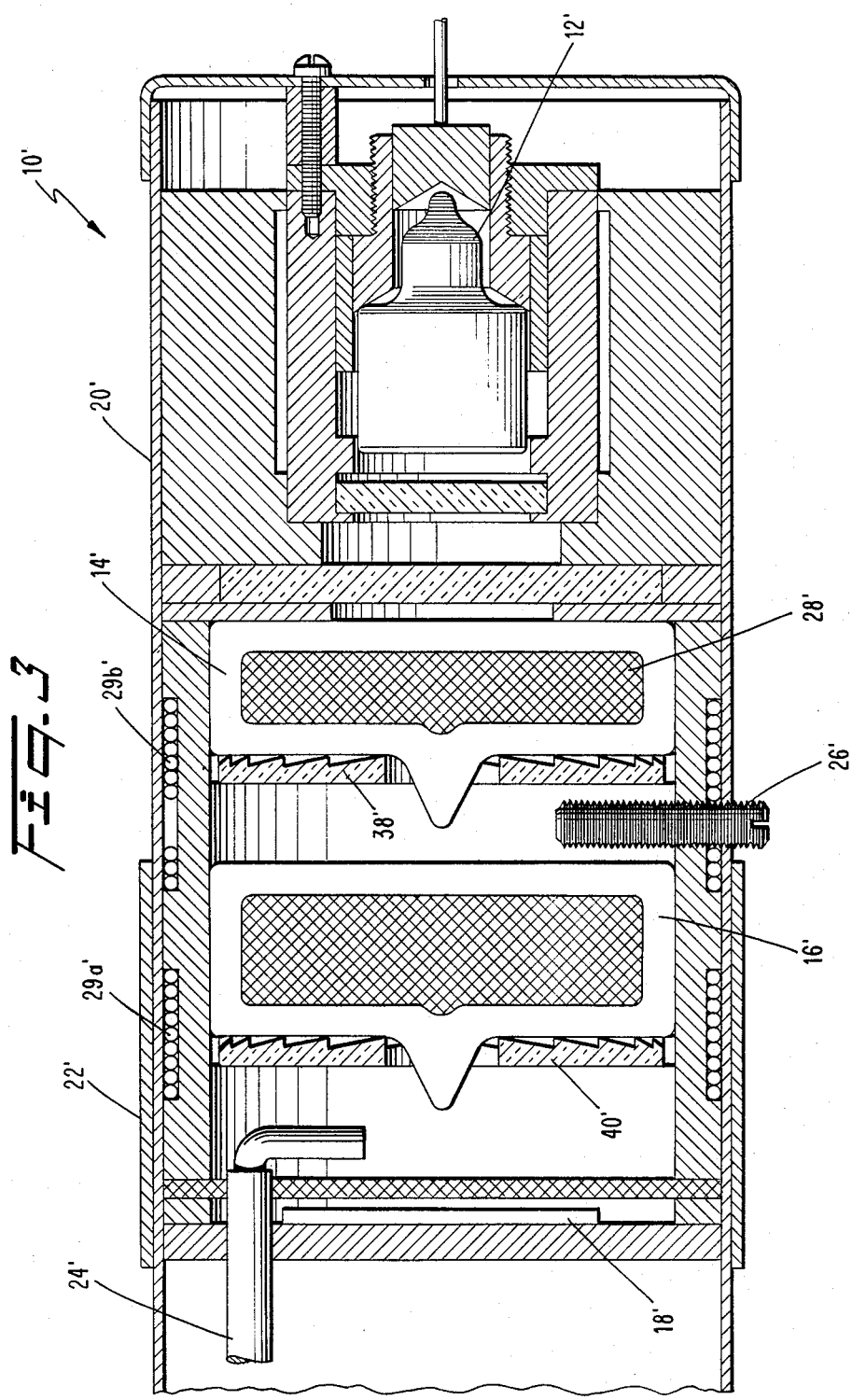
FIG. 3 shows a side view of still another apparatus incorporating the teachings of the present invention.

In FIG. 3 there is illustrated a preferable alternative embodiment of an optical-physics package incorporating the teachings of the present invention wherein elements similar to those shown in FIGS. 1 and 2 are similarly numbered. It should be noted that in FIG. 3, heater 22' is positioned on the external surface of magnetic shield 20' and that turning screw 26' is located between absorption cell 16' and filter cell 28'. It should also be noted that absorption cell 16' and filter cell 28' are end-tubulated.

Figure 4:
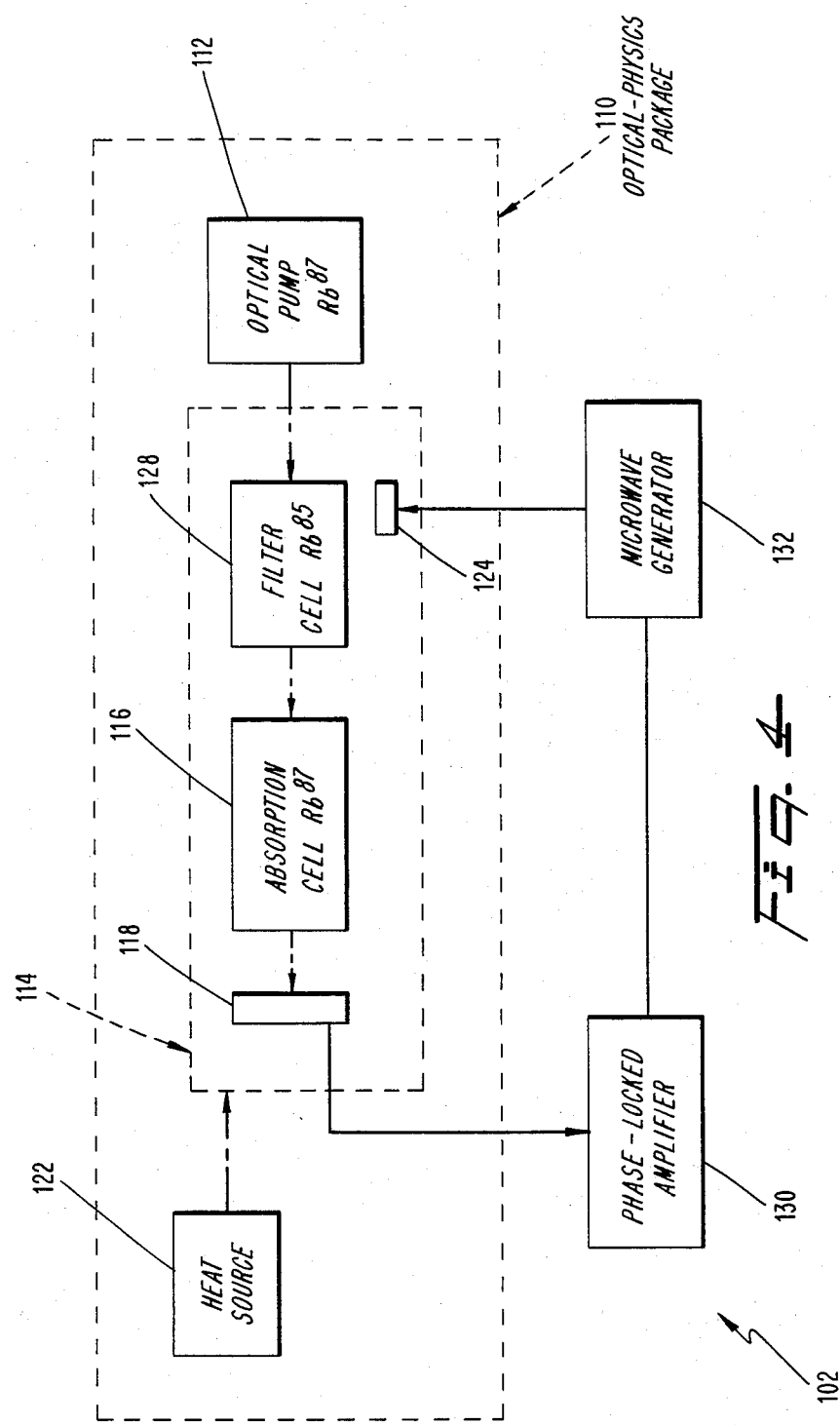
FIG. 4 shows in block diagram form an apparatus incorporating the teachings of the present invention.

In FIG. 4 there is shown, in block diagram form, an atomic frequency standard 102 using the optical-physics package of the subject invention. More specifically, an optical-physics package 110 is provided, including an optical pump or lamp 112, a microwave cavity 114, an absorption cell 116, a light detector or photocell 118, a heat source or heating element 122, a microwave input probe 124, and a filter cell 128. As should be apparent to one skilled in the art, there is also provided in connection with utilization of optical-physics package 110 a phase-locked amplifier 130 and a microwave generator or oscillator 132.

Phase-locked amplifier 130 may, for example, comprise the Princeton Applied Research Model 124A Lock-In Amplifier, or any reasonable equivalent thereto.

The elements of package 110 operate as set forth above. Moreover, generator 132 applies microwave energy to cavity 114 by means of probe 124 to effect relaxation of the $Rb^{87}$ atoms contained within absorption cell 116. Photocell 118 provides an optical sensing means responsive to the output of light from absorption cell 116 whereby the output of photocell 118 may be used by phase-locked amplifier 130 to control the frequency of microwave generator 132.

Various constructions and modifications will become apparent to those skilled in the art in view of the teachings set forth herein, without departing from the spirit or scope of the invention. The invention in its broader aspects is, therefore, not limited to specific details, representative apparatus or the illustrative preferred embodiments shown and described. Thus, it is intended that the present invention cover the various constructions and modifications of this invention, provided they come within the scope of the appended claims and their equivalents.

What is claimed is:

1. In an optical-physics package for use with an atomic frequency standard including a light source, a microwave cavity, and an absorption cell positioned within said cavity to be irradiated by said light source, the improvement comprising a filter cell also positioned within said microwave cavity between said absorption cell and said light source.

2. A package as recited in claim 1 wherein said absorption cell has a temperature coefficient opposite in sign to the temperature coefficient of said filter cell.

3. A package as recited in claim 1 wherein said absorption cell has a temperature coefficient essentially equal in magnitude and opposite in sign to the temperature coefficient of said filter cell.

4. A package as recited in claim 1 further comprising collimating means, located in said cavity between said absorption cell and said filter cell, to uniformly distribute light from said light source onto said absorption cell.

5. A package as recited in claim 1, 2, 3, or 4 wherein said absorption cell and said filter cell are located in sufficiently close physical proximity to one another such that both said cells are subjected to essentially the same temperature fluctuations.

6. A package as recited in claim 1, 2, 3, or 4 wherein said cavity operates in the TE111 mode.

7. A package as recited in claim 1, 2, 3, or 4 wherein the walls of said cavity serve as an oven to provide a temperature within said cavity at which temperature the filter cell achieves a zero light shift condition such that the resonant frequency of said absorption cell is independent of light intensity of the incident light form said light source.

8. An optical-physics package for use with an atomic frequency standard comprising:
   a. a microwave cavity operable in the TE111 mode;
   b. an absorption cell including $Rb^{87}$ and located within said cavity;
   c. light means for illuminating said absorption cell to modify the population density of at least one select energy level of said $Rb^{87}$; and
   d. a filter cell located within said cavity between said light means and said absorption cell, said filter cell including $Rb^{85}$ to attenuate selective energy components of said light means.

9. An optical-physics package of claim 8 wherein said absorption cell has a temperature coefficient opposite in sign to the temperature coefficient of said filter cell.

10. An optical-physics package of claim 8 wherein said absorption cell has a temperature coefficient essentially equal in magnitude and opposite in sign to the temperature coefficient of said filter cell.

11. An optical-physics package of claim 8 further comprising collimating means located in said cavity between said absorption cell and said filter cell to uniformly distribute light from said light source onto said absorption cell.

12. An optical-physics package of claim 8, 9, 10 or 11 wherein said absorption cell and said filter cell are located in sufficiently close physical proximity to one another such that both said cells are subjected to essentially the same temperature fluctuations.

13. A package of claim 1, 2, 3, 4, 8, 9, 10 or 11 wherein said absorption cell and said filter cell include dielectric material for enabling size reduction of said cavity while maintaining frequency resonance within said cavity at the hyperfine transition frequency of the absorption cell.

* * * * *